(12) United States Patent
Delap

(10) Patent No.: US 8,585,748 B2
(45) Date of Patent: Nov. 19, 2013

(54) VACUUM ASSIST DELIVERY SYSTEM

(75) Inventor: Dennis J. Delap, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 176 days.

(21) Appl. No.: 13/198,475

(22) Filed: Aug. 4, 2011

(65) Prior Publication Data

US 2012/0041532 A1 Feb. 16, 2012

Related U.S. Application Data

(60) Provisional application No. 61/373,082, filed on Aug. 12, 2010.

(51) Int. Cl.
*A61F 2/06* (2013.01)

(52) U.S. Cl.
USPC ............................................. 623/1.11

(58) Field of Classification Search
USPC ........ 606/108, 194; 623/1.11–1.2, 1.23, 1.27, 623/2.11
See application file for complete search history.

(56) References Cited

U.S. PATENT DOCUMENTS

| | | | |
|---|---|---|---|
| 4,909,979 A | 3/1990 | Possis et al. | |
| 5,267,954 A * | 12/1993 | Nita | 604/22 |
| 5,628,784 A | 5/1997 | Strecker | |
| 5,690,644 A | 11/1997 | Yurek et al. | |
| 6,165,209 A | 12/2000 | Patterson et al. | |
| 6,562,063 B1 * | 5/2003 | Euteneuer et al. | 623/1.12 |
| 6,656,215 B1 * | 12/2003 | Yanez et al. | 623/1.13 |
| 6,736,839 B2 | 5/2004 | Cummings | |
| 6,818,063 B1 | 11/2004 | Kerrigan | |
| 7,004,926 B2 | 2/2006 | Navia et al. | |
| 7,632,296 B2 | 12/2009 | Malewicz | |
| 7,637,933 B2 * | 12/2009 | Dwyer et al. | 623/1.11 |
| 8,292,947 B2 * | 10/2012 | Hornig | 623/1.21 |
| 8,343,076 B2 * | 1/2013 | Sela et al. | 600/585 |
| 2003/0109837 A1 | 6/2003 | Mcbride-Sakal | |
| 2006/0030923 A1 | 2/2006 | Gunderson | |
| 2006/0095124 A1 | 5/2006 | Benz et al. | |
| 2007/0067011 A1 * | 3/2007 | Krolik et al. | 623/1.11 |
| 2008/0172120 A1 | 7/2008 | Fenn et al. | |
| 2009/0148590 A1 | 6/2009 | Delap | |

FOREIGN PATENT DOCUMENTS

WO   WO 2004/110311 A1   12/2004

* cited by examiner

*Primary Examiner* — Katherine Dowe
*Assistant Examiner* — Amy Shipley
(74) *Attorney, Agent, or Firm* — Brinks Gilson Lione

(57) ABSTRACT

A delivery system for self-expanding medical devices is provided. The delivery system includes seals around an inner catheter. The self-expanding medical device may be mounted on the seals to define an open space between the seals and the inner surface of the medical device and the exterior of the inner catheter. Vacuum pressure may be applied to the open space to reduce friction between the exterior surface of the self-expanding medical device and the inner surface of an outer catheter.

20 Claims, 2 Drawing Sheets

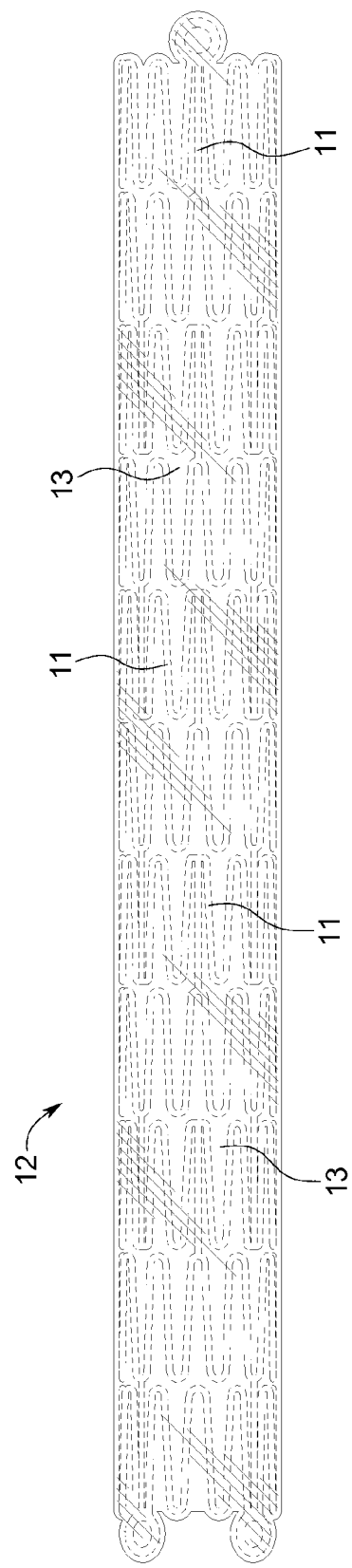

VACUUM ASSIST DELIVERY SYSTEM

This application claims priority to U.S. Provisional Application No. 61/373,082, filed Aug. 12, 2010, which is hereby incorporated by reference herein.

BACKGROUND

The present invention relates generally to medical devices and particularly to delivery systems for self-expanding medical devices.

Minimally invasive medical devices have become relatively common devices for treating numerous organs, such as the vascular system, colon, biliary tract, urinary tract, esophagus, trachea and the like. Stents are one type of minimally invasive medical device that is particularly useful for treating various conditions including occlusions and other related problems that restrict flow through a passage (generally referred to as a stenosis). Stents are also useful for treating various types of aneurysms. Although stents are a well-known type of medical device, many other types of medical devices are used for treating conditions within the human body.

Self-expanding medical devices offer several advantages for treating conditions within a body. In general, self-expanding medical devices are made from spring-like materials, such as stainless steel and nitinol. Typically, self-expanding medical devices have a support structure made from a spring-like material that is compressible into a collapsed configuration. The medical device is usually restrained in the collapsed configuration by a restraint, such as an outer catheter. In a minimally invasive medical device, the collapsed configuration is designed to allow the medical device to be passed through the body in a small profile delivery system that minimizes trauma to the body during the procedure. Once the medical device is positioned at the site in the body where the medical device is intended to be released, the restraint is removed from the medical device, and the spring-like properties of the support structure cause the medical device to expand to a larger configuration. If a medical device is intended to be left in the body for an extended period of time, the delivery system is then withdrawn from the body, and the medical device is left at the site where it was expanded.

One challenge with delivering self-expanding medical devices is that the medical device exerts outward force against the restraint when the medical device is in the collapsed configuration due to the spring-like properties of the support structure. This can make it difficult to remove the restraint at the implantation site. For example, in one type of delivery system where the restraint is an outer catheter that is withdrawn from the medical device, the medical device typically exerts outward force against the inner surface of the outer catheter. This creates friction between the medical device and the outer catheter that must be overcome in order to release the medical device. Friction between the medical device and the restraint can be particularly high for medical devices that are especially long; for medical devices with coatings or graft layers with higher friction coefficients; and for restraints that do not have low friction coefficients.

Because of the tension and/or friction that occurs between a self-expanding medical device and its restraint, self-expanding medical device delivery systems suffer from a number of problems. In some cases, the amount of force that may be needed to overcome the friction between the medical device and its restraint can be so high that a physician cannot release the medical device at the implantation site. The high forces needed to deliver self-expanding medical devices can also contribute to inaccurate placement of the medical device due to inadvertent movements of the delivery system that occur when the physician is attempting to overcome the delivery forces. Damage can also occur to parts of the medical device, such as the support structure, coatings and/or graft layers. It is also possible that the restraint can be damaged when trying to remove the restraint from the medical device.

Accordingly, the inventor believes it would be desirable to provide a self-expanding medical device delivery system with lower delivery forces.

SUMMARY

A medical device delivery system is described that may be used to reduce the force required to deploy a medical device. The delivery system includes circumferential seals attached to an inner catheter. The medical device is mounted on the seals. Vacuum pressure may be applied to an open space between the seals to pull the medical device partially into the open space.

The invention may include any of the following aspects in various combinations and may also include any other aspect described below in the written description or in the attached drawings.

A medical device delivery system, comprising:
an inner catheter comprising a first port opening to an exterior of the inner catheter, the first port being in fluid communication with a proximal end of the inner catheter;
a first seal attached to an exterior surface of the inner catheter, the first seal being disposed proximally from the first port;
a second seal attached to the exterior surface of the inner catheter, the second seal being disposed distally from the first port;
a self-expanding medical device in a collapsed configuration mounted around the inner catheter, the first and second seals contacting an inner surface of the medical device and thereby sealing the medical device to the inner catheter, the self-expanding medical device comprising a graft layer extending between the first and second seals and fully covering the medical device between the first and second seals, a first open space being disposed between the inner surface of the medical device and the exterior surface of the inner catheter between the first and second seals; and
wherein the first and second seals are capable of maintaining a vacuum applied by the first port within the first open space, the medical device thereby collapsing at least partially into the first open space.

The medical device delivery system further comprising an outer catheter disposed around the medical device, the medical device expanding outward against the outer catheter and the outer catheter restraining the medical device in the collapsed configuration.

The medical device delivery system further comprising a vacuum lumen extending through the inner catheter from the first port to the proximal end of the inner catheter.

The medical device delivery system further comprising:
a third seal attached to the exterior surface of the inner catheter, the third seal being disposed distally from the second seal;
the third seal contacting the inner surface of the medical device and thereby sealing the medical device to the inner catheter, the graft layer extending between the first and third seals and fully covering the medical device between the first and third seals, a second open space being disposed between the inner surface of the medical device and the exterior surface of the inner catheter between the second seal and the third seal;

the inner catheter further comprising a second port opening to the exterior of the inner catheter, the second port being in fluid communication with a proximal end of the inner catheter;

a first vacuum lumen extending through the inner catheter from the first port to the proximal end of the inner catheter;

a second vacuum lumen extending through the inner catheter from the second port to the proximal end of the inner catheter; and wherein the second and third seals are capable of maintaining a vacuum applied by the second port within the second open space, the medical device thereby collapsing at least partially into the second open space, the first and second vacuum lumens being isolated from each other and the first and second ports being isolated from each other, the first and second vacuum lumens thereby providing independent vacuums applied to the first and second open spaces.

The medical device delivery system further comprising an outer catheter disposed around the medical device, the medical device expanding outward against the outer catheter and the outer catheter restraining the medical device in the collapsed configuration.

The medical device delivery system wherein the inner catheter comprises an inner lumen, and further comprising:

a control catheter disposed within the inner lumen, the control catheter comprising a second port opening to an exterior of the control catheter, the second port being in fluid communication with a proximal end of the control catheter;

a third seal attached to an exterior surface of the control catheter, the third seal being disposed proximally from the second port;

a fourth seal attached to the exterior surface of the control catheter, the fourth seal being disposed distally from the second port;

the third and fourth seals contacting the inner lumen of the inner catheter and thereby sealing the inner catheter to the control catheter;

the control catheter being slidable relative to the inner catheter from a first position where the third seal is disposed proximally of the first port and the fourth seal is disposed distally of the first port, the first and second ports being in fluid communication with each other in the first position to maintain a vacuum between the first and second ports, and a second position where the third seal is disposed distally of the first port or the fourth seal is disposed proximally of the first port, the first and second ports not being in fluid communication with each other in the second position to disconnect the vacuum between the first and second ports.

The medical device delivery system further comprising a plurality of the first and second seals and a plurality of the first port, each of the first ports being disposed between one of the first seals and one of the second seals, wherein the third seal is disposed proximally of all of the first ports and the fourth seal is disposed distally of all of the first ports in the first position, and the third seal is disposed distally of at least one of the first ports or the fourth seal is disposed proximally of at least one of the first ports in the second position.

The medical device delivery system further comprising an outer catheter disposed around the medical device, the medical device expanding outward against the outer catheter and the outer catheter restraining the medical device in the collapsed configuration.

A method of delivering a medical device, comprising:

applying a vacuum to a first vacuum lumen, the first vacuum lumen being in fluid communication with a first port opening to an exterior of an inner catheter, a first seal being attached to an exterior surface of the inner catheter and being disposed proximally from the first port, a second seal being attached to the exterior surface of the inner catheter and being disposed distally from the first port, a self-expanding medical device in a collapsed configuration being mounted around the inner catheter and the first and second seals contacting an inner surface of the medical device thereby sealing the medical device to the inner catheter, the self-expanding medical device comprising a graft layer extending between the first and second seals and fully covering the medical device between the first and second seals, a first open space being disposed between the inner surface of the medical device and the exterior surface of the inner catheter between the first and second seals, the vacuum collapsing the medical device at least partially into the first open space;

sliding the medical device and an outer sheath disposed about the medical device relative to each other while the vacuum is applied to the first vacuum lumen, the medical device thereby being moved toward a distal end of the outer catheter; and reducing the vacuum to release the medical device from the first and second seals, the medical device self-expanding away from the first and second seals into a body.

The method further comprising:

applying another vacuum to a second vacuum lumen, the second vacuum lumen being in fluid communication with a second port opening to the exterior of the inner catheter, a third seal being attached to the exterior surface of the inner catheter and being disposed distally from the second seal, the third seal contacting the inner surface of the medical device thereby sealing the medical device to the inner catheter, the graft layer extending between the first and third seals and fully covering the medical device between the first and third seals, a second open space being disposed between the inner surface of the medical device and the exterior surface of the inner catheter between the second and third seals, the vacuum collapsing the medical device at least partially into the second open space, the first and second vacuum lumens being isolated from each other and the first and second ports being isolated from each other; and reducing the another vacuum to release the medical device from the second and third seals, the medical device self-expanding away from the second and third seals into the body, wherein the vacuum and the another vacuum are reduced at different times from each other.

The method wherein the vacuum is reduced by sliding a control catheter relative to the inner catheter, the control catheter being disposed within an inner lumen of the inner catheter, the first vacuum lumen extending through the control catheter and opening at a second port to an exterior of the control catheter, a third seal being attached to the exterior surface of the control catheter and being disposed proximally from the second port, a fourth seal being attached to the exterior surface of the control catheter and being disposed distally from the second port, the third and fourth seals contacting the inner lumen of the inner catheter thereby sealing the inner catheter to the control catheter, a first position of the control catheter disposing the third seal proximally of the first port and disposing the fourth seal distally of the first port, the first and second ports being in fluid communication with each other in the first position to maintain the vacuum, and a second position of the control catheter disposing the third seal distally of the first port or disposing the fourth seal proximally of the first port, the first and second ports not being in fluid communication with each other in the second position to disconnect the vacuum between the first and second ports.

The method further comprising maintaining the vacuum on at least one of the first port while reducing the vacuum on at least another of the first port to release a portion of the medical device, each of the first ports being disposed between one of the first seals and one of the second seals, the third seal being disposed proximally of all of the first ports and the fourth seal being disposed distally of all of the first ports in the first position, and the third seal being disposed distally of the another of the first ports or the fourth seal being disposed proximally of the another of the first ports in the second position.

BRIEF DESCRIPTION OF SEVERAL VIEWS OF THE DRAWINGS

The invention may be more fully understood by reading the following description in conjunction with the drawings, in which:

FIG. 2 is a side view of a stent-graft;

DETAILED DESCRIPTION

Figure 1:
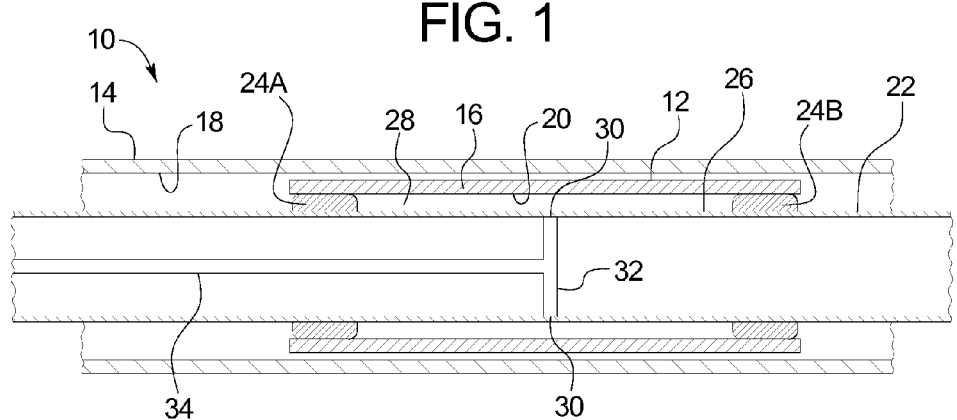
FIG. 1 is a cross-sectional view of a self-expanding medical device delivery system.

Referring now to the figures, and particularly to FIG. 1, a self-expanding medical device delivery system 10 is shown. Although the delivery systems 10, 36, 40 described herein may be used to deliver other types of medical devices into a body, the medical device 12 shown in the figures is a stent 12. As those in the art understand, a stent 12 usually has a cylindrical structure that is expandable from a collapsed configuration to an expanded configuration. As shown in FIG. 2, the stent structure 12 may be made from a series of interconnected struts 11 that compress towards each other in the collapsed configuration and expand away from each other in the expanded configuration. Preferably, the medical device 12 is a self-expanding medical device 12, which means that the structure of the medical device 12 is made from a spring-like material. In the case of a stent 12, the stent structure 12 is relaxed, or unstressed, in the expanded configuration. The stent 12 is then stressed to compress it into the collapsed configuration shown in FIG. 1. Normally, the stent 12 is restrained by an outer catheter 14 in order to maintain the stent 12 in the collapsed configuration. In the restrained state, the exterior surface 16 of the stent 12 presses outward against the inner surface 18 of the outer catheter 14. The outer catheter 14 may be a catheter 14 that is passed to the treatment site together with the stent 12, thereby maintaining the relative positions of the stent 12 and the outer catheter 14 as they move together through the body. The outer catheter 14 may also be a guiding catheter 14 that is passed to the treatment site first, after which the stent 12 is passed through the outer catheter 14 to reach the treatment site.

As described below, the medical device delivery systems 10, 36, 40 use vacuum pressure to minimize outward pressure between the stent 12 and the outer catheter 14. Therefore, in order for the vacuum pressure to effectively draw the stent 12 or other medical device 12 away from the inner surface 18 of the outer catheter 14, the wall of the stent 12 must generally be impermeable to the vacuum pressure when the stent 12 is in the collapsed configuration. As shown in FIG. 2, this may be accomplished by providing the stent 12 with a graft layer 13 that fully covers at least part of the stent 12. The graft layer 13 has a minimum porosity that resists flow through the graft layer 13 when the vacuum pressure is applied to the inner surface 20 of the stent 12. For example, graft layers 13, such as Thoralon or ePTFE, may be desirable. Thus, the graft layer 13 covers the open spaces between the struts 11 in the stent structure 12 to prevent flow through the struts 11.

As shown in FIG. 1, the stent 12 is mounted around an inner catheter 22. At least two seals 24, or first 24A and second 24B seals, are attached to the exterior surface 26 of the inner catheter 22 and extend circumferentially around the inner catheter 22. This seals 24 may be attached to the inner catheter 22 by gluing or by other known methods. The stent 12 is mounted on and contacts the seals 24. Thus, the stent 12 may be slightly spaced away from the exterior surface 26 of the inner catheter 22 so that an open space 28 is formed between the inner surface 20 of the stent 12 and the exterior surface 26 of the inner catheter 22 and between the first 24A and second 24B seals. Although the seals 24 may be positioned differently than shown, it is preferable for one seal 24 to be at each end of the stent 12. The seals 24 are preferably made from a rubber-like material with elastomeric properties in order to seal against the stent 12. For example, silicone gel, silicone rubber, or EPDM rubber may be preferable. It may also be preferable for the material of the seals 24 to have a durometer of about 40-50 Shore A.

The first seal 24A is positioned on the inner catheter 22 proximally from a port 30, and the second seal 24B is positioned on the inner catheter 22 distally from the port 30. Thus, the port 30 opens to the exterior surface 26 of the inner catheter 22 within the open space 28. The inner catheter 22 may include multiple ports 30. For example, as shown in FIG. 1, two ports 30 may be positioned on opposite sides of the inner catheter 22 and may be interconnected by a radial lumen 32. The radial lumen 32 may be interconnected with a longitudinal lumen 34 that extends to the proximal end of the inner catheter 22. Although the inner catheter 22 may be manufactured in various ways, the inner catheter 22 may be made by bonding or welding a hollow tube as the proximal portion to a solid shaft as the distal portion. The wall of the hollow tube may then be punctured to form the port 30, with the hollow tube providing fluid communication to the proximal end of the inner catheter 22.

The delivery system 10 is particularly useful for delivering a self-expanding medical device 12, such as a stent 12, and minimizing outward pressure between the medical device 12 and an outer catheter 14. As in a conventional self-expanding medical device delivery system, the outer catheter 14 may be used to restrain the stent 12 in the collapsed configuration. Thus, the exterior surface 16 of the stent 12 presses outward against the inner surface 18 of the outer catheter 14. A vacuum may be applied to the longitudinal lumen 34, which conveys the vacuum pressure to the radial lumen 32, the ports 30 and the open space 28. Because the open space 28 is generally sealed by the seals 24 and the stent 12, the vacuum pressure pulls the stent 12 inward into the open space 28 and toward the inner catheter 22. As a result, the stent 12 is pulled away from the inner surface 18 of the outer catheter 14. For example, for a typical stent 12 that is covered by a graft layer 13 and is 8 mm in diameter and 80 mm long, the outward force of the stent 12 against the outer catheter 14 may be about 10 lbs. In order to equalize this outward force, a vacuum pressure of about 3.2 psi may be used to counteract the outward force. The type of vacuum pressure that is applied and the amount of pressure may be varied as desired. Since the vacuum pressure is essentially trying to suck fluid into the vacuum lumens 32, 34. It is possible that a small amount of leakage through the seals 24 and the stent structure 12 may be acceptable, since this would result in blood being sucked into the vacuum lumens 32, 34, which may not be deemed a problem. Since the vacuum pressure is a sucking force, the vacuum pressure may be a gas, since the gas would be sucked out through the vacuum lumens 32, 34 and could be prevented from escaping into the body. However, the vacuum pressure could also be applied using a fluid, such as saline, if concerns of gas escaping into the body exists.

Figure 4:
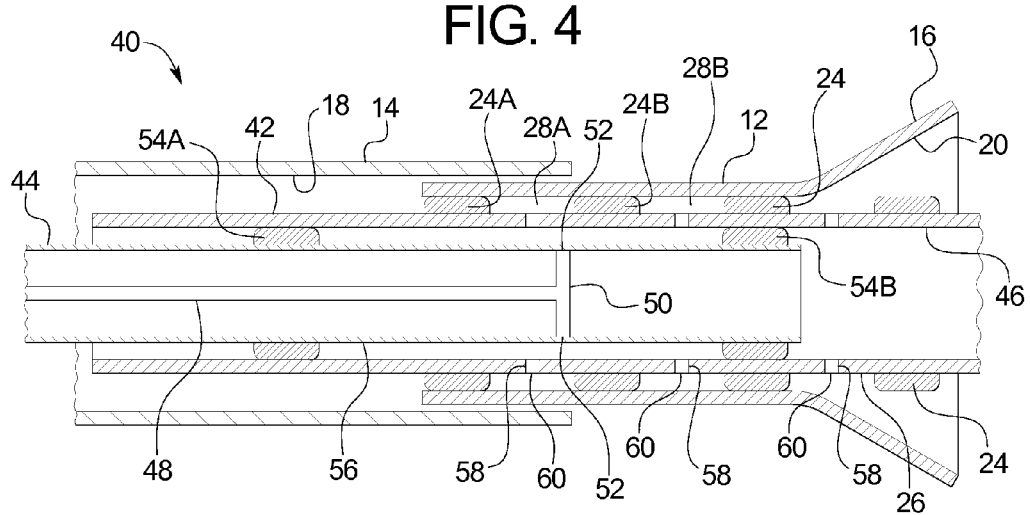
FIG. 4 is a cross-sectional view of another self-expanding medical device delivery system.

After the vacuum pressure has been applied, the inner catheter 22 and stent 12 may be slid relative to the outer catheter 14 without encountering significant friction between the outer catheter 14 and the stent 12. For example, as shown in FIG. 4, the outer catheter 14 may be slid proximally while the inner catheter 22 and stent 12 remain fixed in place at the treatment site. After the outer catheter 14 is no longer restraining the stent 12 or no longer restraining part of the stent 12, the vacuum pressure may be reduced or stopped altogether. As a result, the stent 12 is released from the seals 24 and self-expands into the body. Once the stent 12 is fully released from the outer catheter 14 and inner catheter 22. The inner and outer catheters 22, 14 are removed from the body and the medical device 12 may be left implanted at the treatment site.

Figure 3:
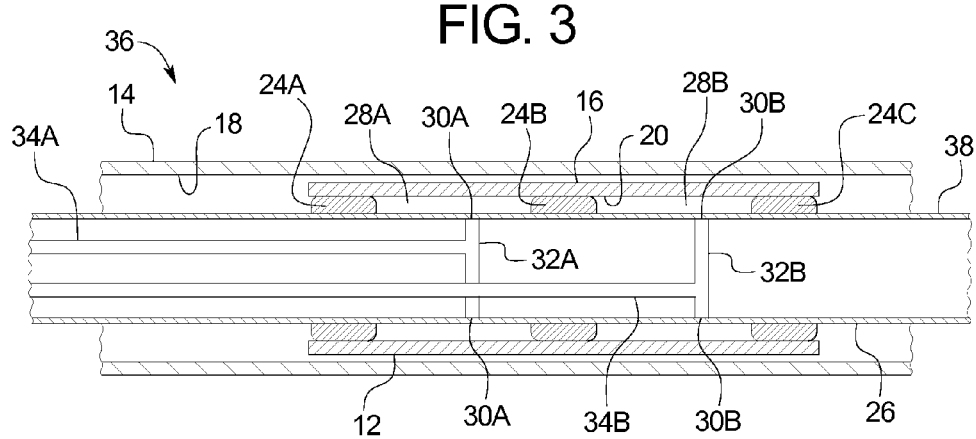
FIG. 3 is a cross-sectional view of another self-expanding medical device delivery system.

As shown in FIG. 3, the delivery system 36 may be provided with multiple seals 24 and ports 32 to segment the vacuum system along the length of the stent 12. Although more segments may be provided, the embodiment shown in FIG. 3 has two open spaces 28 between the inner surface 20 of the stent 12 and the exterior surface 26 of the inner catheter 38. The first open space 28A is defined by the first seal 24A and the second seal 24B. The second open space 28B is defined by the second seal 24B and the third seal 24C. Vacuum pressure is supplied to the first open space 28A by a first longitudinal lumen 34A, first radial lumen 32A and first ports 30A. Vacuum pressure is supplied to the second open space 28B by a second longitudinal lumen 34B, second radial lumen 32B and second ports 30B. The first 32A, 34A and second 32B, 34B lumens, and ports 30A, 30B, are isolated from each other so that a different vacuum pressure can be applied to the first open space 28A and the second open space 28B.

One advantage of the embodiment of FIG. 3 is that different segments of the stent 12 can be released at different times. For example, although the first 32A, 34A and second 32B, 34B lumens are isolated from each other, a similar vacuum pressure can be applied to both of the first 28A and second 28B open spaces initially. As explained above, this can be used to reduce the friction between the exterior surface 16 of the stent 12 and the inner surface 18 of the outer catheter 14. The outer catheter 14 may then be slid proximally relative to the stent 12. When the distal end of the stent 12 is uncovered by the outer catheter 14, the vacuum pressure to the second open space 28B can be reduced to release this distal end of the stent 12. At the same time, the vacuum pressure on the first open space 28A can be maintained to pull the proximal end of the stent 12 inward away from the outer catheter 14 and prevent friction at the proximal end. The outer catheter 14 can then be slid proximally farther until the stent 12 is uncovered further or entirely. The vacuum pressure on the first open space 28A can then be reduced to release the proximal end of the stent 12. Alternatively, the outer catheter 14 can be fully withdrawn from the stent 12 while vacuum pressure is maintained on both the first 28A and second 28B open spaces. The vacuum pressure can then be reduced at the open spaces 28 at different times to control expansion of the stent 12 into the body as desired.

As shown in FIG. 4, the vacuum pressure can also be reduced to multiple open spaces 28 with a single vacuum source provided through the lumens 48, 50, 58 and ports 52, 60. In this delivery system 40, the inner catheter 42 is provided with a control catheter 44 inside an inner lumen 46 of the inner catheter 42. A single longitudinal lumen 48 extends through the control catheter 44 to provide vacuum pressure to the radial lumen 50 and second ports 52. Third 54A and forth 54B seals are attached to the exterior surface 56 of the control catheter 44 and extend circumferentially around the control catheter 44. The third seal 54A is positioned proximally from the second ports 52, and the fourth seal 54B is positioned distally from the second ports 52. The third and fourth seals 54 contact the inner lumen 46 of the inner catheter 42 and seal the inner catheter 42 to the control catheter 44. The inner catheter 42 has a plurality of radial lumens 58 extending through the wall of the inner catheter 42. The radial lumens 58 through the inner catheter 42 define a plurality of first ports 60 that open to a plurality of open spaces 28. Each of the open spaces 28 are defined by first and second seals 24 attached to the exterior surface 26 of the inner catheter 42 that seal against the medical device 12. Preferably, the third and fourth seals 54 are spaced away from each other far enough so that all of the first ports 60 can be initially positioned between the third and fourth seals 54. Although similar material as used for the first and second seals 24 may be used for the third and fourth seals 54, it may be preferable for the third and fourth seals 54 to be tougher and harder than the first and second seals 24. For example, the third and fourth seals 54 may have a durometer of about 50-60 Shore A.

The delivery system 40 of FIG. 4 may be used by maintaining a constant vacuum pressure on the longitudinal lumen 48, radial lumen 50 and second ports 52. Initially, the vacuum pressure is applied to all of the open spaces 28, since all of the first ports 60 are positioned between the third and fourth seals 54. Thus, each segment of the stent 12 is pulled partially into the respective open space 28. As explained above, this pulls the stent 12 away from the inner surface 18 of the outer catheter 14 to minimize friction between the stent 12 and outer catheter 14. The outer catheter 14 can then be slid relative to the inner catheter 42 and stent 12. In order to release the stent 12, the control catheter 44 can be slid relative to the inner catheter 42. For example, as shown in FIG. 4, the control catheter 44 may be pulled proximally until the fourth seal 54B passes the most distal first port 60. As a result, the vacuum pressure is disconnected from the most distal first port 60, since the vacuum pressure is only maintained between the third and fourth seals 54. This allows the distal end of the stent 12 to release and self-expand into the body. However, the vacuum pressure is maintained at the remaining first ports 60 and open spaces 28. The control catheter 44 may then be withdrawn proximally to disconnect the vacuum pressure from the remaining open spaces 28 as desired. As explained above, the vacuum pressure may be disconnected from the open spaces 28 as segments are uncovered by the outer catheter 14. Alternatively, the outer catheter 14 can be removed entirely from the stent 12 first and the vacuum pressure can be disconnected from the open spaces 28 using the control catheter 44 in the manner desired.

Alternatively, the delivery system of FIG. 4 may be used with the inner catheter 38 of FIG. 3 in place of the control catheter 44 shown in FIG. 4. In this alternative embodiment, ambient pressure may be applied to the second ports 30B while vacuum pressure may be applied to the first ports 30A. In order to release the stent 12, the inner catheter 38 may be positioned so that the second ports 30B are in communication with the most distal first ports 60. In this position, the vacuum pressure on the remaining first ports 60 will retain the proximal end of the stent 12 on the inner catheter 42. However, the ambient pressure at the second ports 30B will release the distal end of the stent 12 at the most distal first ports 60. Advantages of this approach are that saline may be provided as the ambient fluid pressure at the second ports 30B, which may provide improved control over the release of the stent 12, and preselected fluids may be used at the release ports instead of bodily fluids.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A medical device delivery system, comprising:
    an inner catheter comprising a first port opening to an exterior of said inner catheter, said first port being in fluid communication with a proximal end of said inner catheter;
    a first seal attached to an exterior surface of said inner catheter, said first seal being disposed proximally from said first port;
    a second seal attached to said exterior surface of said inner catheter, said second seal being disposed distally from said first port;
    a self-expanding medical device in a collapsed configuration mounted around said inner catheter, said first and second seals contacting an inner surface of said medical device and thereby sealing said medical device to said inner catheter, said self-expanding medical device comprising a graft layer extending between said first and second seals and fully covering said medical device between said first and second seals, a first open space being disposed between said inner surface of said medical device and said exterior surface of said inner catheter between said first and second seals; and
    wherein said first and second seals maintain a vacuum applied by said first port within said first open space, said medical device being retained in a collapsed configuration and collapsing at least partially into said first open space in response to said vacuum.

2. The medical device delivery system according to claim 1, further comprising an outer catheter disposed around said medical device, said medical device expanding outward against said outer catheter and said outer catheter restraining said medical device in said collapsed configuration.

3. The medical device delivery system according to claim 1, further comprising a vacuum lumen extending through said inner catheter from said first port to said proximal end of said inner catheter.

4. The medical device delivery system according to claim 1, further comprising:
    a third seal attached to said exterior surface of said inner catheter, said third seal being disposed distally from said second seal;
    said third seal contacting said inner surface of said medical device and thereby sealing said medical device to said inner catheter, said graft layer extending between said first and third seals and fully covering said medical device between said first and third seals, a second open space being disposed between said inner surface of said medical device and said exterior surface of said inner catheter between said second seal and said third seal;
    said inner catheter further comprising a second port opening to said exterior of said inner catheter, said second port being in fluid communication with a proximal end of said inner catheter;
    a first vacuum lumen extending through said inner catheter from said first port to said proximal end of said inner catheter;
    a second vacuum lumen extending through said inner catheter from said second port to said proximal end of said inner catheter; and
    wherein said second and third seals are capable of maintaining a vacuum applied by said second port within said second open space, said medical device thereby collapsing at least partially into said second open space, said first and second vacuum lumens being isolated from each other and said first and second ports being isolated from each other, said first and second vacuum lumens thereby providing independent vacuums applied to said first and second open spaces.

5. The medical device delivery system according to claim 4, further comprising an outer catheter disposed around said medical device, said medical device expanding outward against said outer catheter and said outer catheter restraining said medical device in said collapsed configuration.

6. The medical device delivery system according to claim 5, wherein said self-expanding medical device is a stent, and said first, second and third seals comprise an elastomeric rubber-like material.

7. The medical device delivery system according to claim 1, wherein said inner catheter comprises an inner lumen, and further comprising:
    a control catheter disposed within said inner lumen, said control catheter comprising a second port opening to an exterior of said control catheter, said second port being in fluid communication with a proximal end of said control catheter;
    a third seal attached to an exterior surface of said control catheter, said third seal being disposed proximally from said second port;
    a fourth seal attached to said exterior surface of said control catheter, said fourth seal being disposed distally from said second port;
    said third and fourth seals contacting said inner lumen of said inner catheter and thereby sealing said inner catheter to said control catheter;
    said control catheter being slidable relative to said inner catheter from a first position where said third seal is disposed proximally of said first port and said fourth seal is disposed distally of said first port, said first and second ports being in fluid communication with each other in said first position to maintain a vacuum between said first and second ports, and a second position where said third seal is disposed distally of said first port or said fourth seal is disposed proximally of said first port, said first and second ports not being in fluid communication with each other in said second position to disconnect said vacuum between said first and second ports.

8. The medical device delivery system according to claim 7, further comprising a plurality of said first and second seals and a plurality of said first port, each of said first ports being disposed between one of said first seals and one of said second seals, wherein said third seal is disposed proximally of all of said first ports and said fourth seal is disposed distally of all of said first ports in said first position, and said third seal is disposed distally of at least one of said first ports or said fourth seal is disposed proximally of at least one of said first ports in said second position.

9. The medical device delivery system according to claim 8, further comprising an outer catheter disposed around said medical device, said medical device expanding outward against said outer catheter and said outer catheter restraining said medical device in said collapsed configuration.

10. The medical device delivery system according to claim 9, wherein said self-expanding medical device is a stent, and said first and second seals comprise an elastomeric rubber-like material, and said third and fourth seals comprise a material that is tougher and harder than the material of the first and second seals.

11. The medical device delivery system according to claim 1, wherein said self-expanding medical device is a stent.

12. The medical device delivery system according to claim 1, wherein said graft layer comprises Thoralon or ePTFE.

13. The medical device delivery system according to claim 1, wherein said first and second seals comprise an elastomeric rubber-like material.

14. The medical device delivery system according to claim 13, wherein said first and second seals comprise silicone gel, silicone rubber, or EPDM rubber.

15. The medical device delivery system according to claim 1, wherein said first and second seals have a durometer of about 40-50 Shore A.

16. The medical device delivery system according to claim 1, further comprising an outer catheter disposed around said medical device, said medical device expanding outward against said outer catheter and said outer catheter restraining said medical device in said collapsed configuration, and a vacuum lumen extending through said inner catheter from said first port to said proximal end of said inner catheter, wherein said self-expanding medical device is a stent, and said first and second seals comprise an elastomeric rubber-like material.

17. A method of delivering a medical device, comprising:
applying a vacuum to a first vacuum lumen, said first vacuum lumen being in fluid communication with a first port opening to an exterior of an inner catheter, a first seal being attached to an exterior surface of said inner catheter and being disposed proximally from said first port, a second seal being attached to said exterior surface of said inner catheter and being disposed distally from said first port, a self-expanding medical device in a collapsed configuration being mounted around said inner catheter and said first and second seals contacting an inner surface of said medical device thereby sealing said medical device to said inner catheter, said self-expanding medical device comprising a graft layer extending between said first and second seals and fully covering said medical device between said first and second seals, a first open space being disposed between said inner surface of said medical device and said exterior surface of said inner catheter between said first and second seals, said vacuum collapsing said medical device at least partially into said first open space;
sliding said medical device and an outer sheath catheter disposed about said medical device relative to each other while said vacuum is applied to said first vacuum lumen, said medical device thereby being moved toward a distal end of said outer catheter; and
reducing said vacuum to release said medical device from said first and second seals, said medical device self-expanding away from said first and second seals into a body.

18. The method according to claim 17, further comprising:
applying another vacuum to a second vacuum lumen, said second vacuum lumen being in fluid communication with a second port opening to said exterior of said inner catheter, a third seal being attached to said exterior surface of said inner catheter and being disposed distally from said second seal, said third seal contacting said inner surface of said medical device thereby sealing said medical device to said inner catheter, said graft layer extending between said first and third seals and fully covering said medical device between said first and third seals, a second open space being disposed between said inner surface of said medical device and said exterior surface of said inner catheter between said second and third seals, said vacuum collapsing said medical device at least partially into said second open space, said first and second vacuum lumens being isolated from each other and said first and second ports being isolated from each other; and
reducing said another vacuum to release said medical device from said second and third seals, said medical device self-expanding away from said second and third seals into said body, wherein said vacuum and said another vacuum are reduced at different times from each other.

19. The method according to claim 17, wherein said vacuum is reduced by sliding a control catheter relative to said inner catheter, said control catheter being disposed within an inner lumen of said inner catheter, said first vacuum lumen extending through said control catheter and opening at a second port to an exterior of said control catheter, a third seal being attached to said exterior surface of said control catheter and being disposed proximally from said second port, a fourth seal being attached to said exterior surface of said control catheter and being disposed distally from said second port, said third and fourth seals contacting said inner lumen of said inner catheter thereby sealing said inner catheter to said control catheter, a first position of said control catheter disposing said third seal proximally of said first port and disposing said fourth seal distally of said first port, said first and second ports being in fluid communication with each other in said first position to maintain said vacuum, and a second position of said control catheter disposing said third seal distally of said first port or disposing said fourth seal proximally of said first port, said first and second ports not being in fluid communication with each other in said second position to disconnect said vacuum between said first and second ports.

20. The method according to claim 19, further comprising a plurality of said first and second seals and a plurality of said first port, and maintaining said vacuum on at least one of said first ports while reducing said vacuum on at least another of said first ports to release a portion of said medical device, each of said first ports being disposed between one of said first seals and one of said second seals, said third seal being disposed proximally of all of said first ports and said fourth seal being disposed distally of all of said first ports in said first position, and said third seal being disposed distally of said another of said first ports or said fourth seal being disposed proximally of said another of said first ports in said second position.

* * * * *